United States Patent [19]

Zweben

[11] 4,213,755
[45] Jul. 22, 1980

[54] MERCURY VAPOR PURIFIER ENCLOSURE

[76] Inventor: Leon L. Zweben, 1015 Forest Ave., Lakewood, N.J. 08701

[21] Appl. No.: 972,244

[22] Filed: Dec. 22, 1978

[51] Int. Cl.³ .............................................. A61C 19/00
[52] U.S. Cl. .................................................... 433/49
[58] Field of Search ........................... 128/1 B; 312/1; 32/60 R; 433/49

[56] References Cited

U.S. PATENT DOCUMENTS

| | | | |
|---|---|---|---|
| 2,708,927 | 5/1955 | Dixon et al. | 128/1.8 |
| 3,971,644 | 7/1976 | Sugarman | 312/1 |
| 4,108,509 | 8/1978 | Piet | 32/60 A |

*Primary Examiner*—Robert Peshock
*Attorney, Agent, or Firm*—Arthur L. Plevy

[57] ABSTRACT

An enclosure is provided for use in handling hazardous materials such as mercury. The enclosure includes a hollow housing having an opened bottom end. The walls of the housing are preferably fabricated from a clear plastic to provide unobstructed visibility. A bottom platform is provided for a work area and the opened bottom of the housing fits within the platform. A fan and filter unit is mounted in the top wall of the housing via an aperture to enable air to be drawn from the housing through the filter by the action of the fan. The air is filtered prior to discharge into the atmosphere to rid the same of mercury or obnoxious vapors. The internal hollow of the housing is accessed by means of a pair of ports located on a front wall of the housing. The ports are blocked by means of elastic bands which are flexed when a user's hands are inserted through the apertures to allow access to an amalgamator or other devices contained within the housing.

10 Claims, 6 Drawing Figures

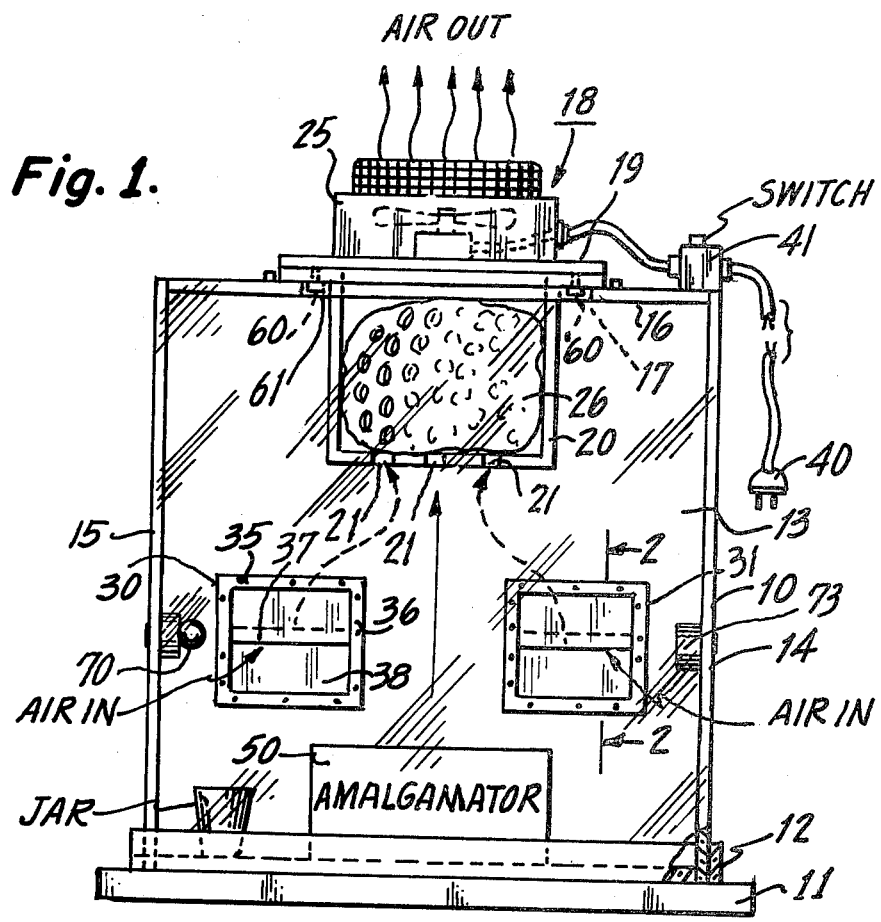
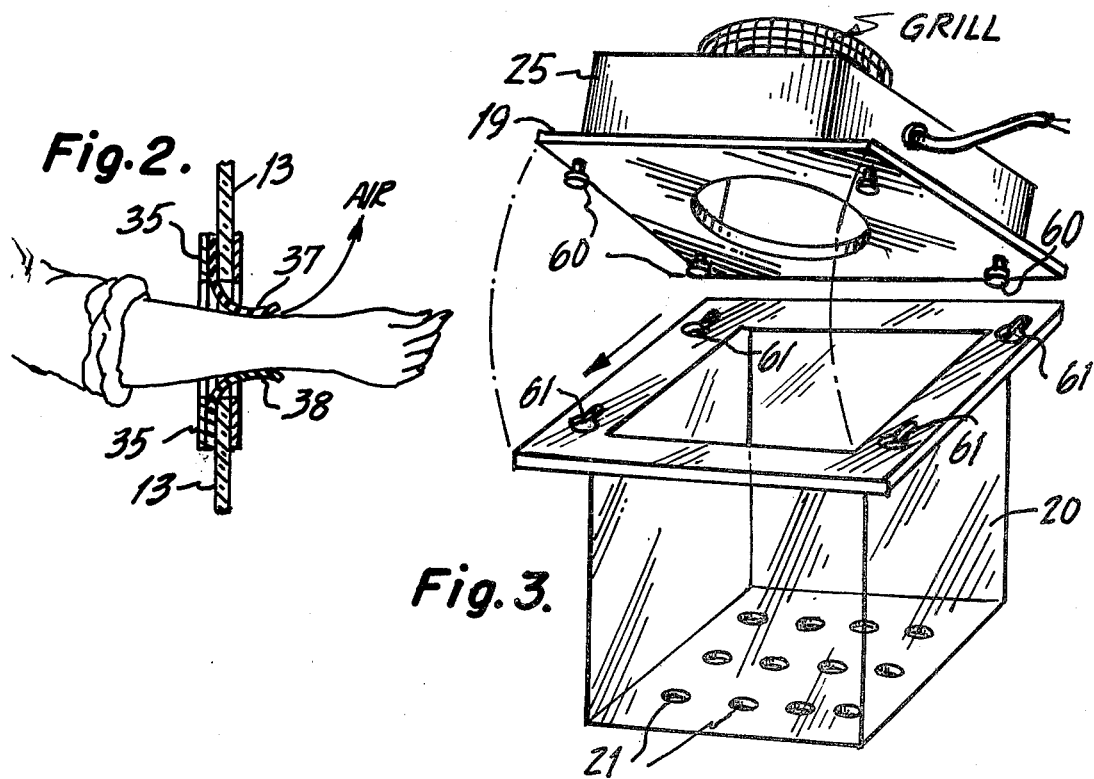

MERCURY VAPOR PURIFIER ENCLOSURE

BACKGROUND OF THE INVENTION

This invention relates to an environmental enclosure for handling hazardous materials and more particularly to a mercury vapor purifier enclosure for use in dental establishments for working with and handling amalgam.

The hazards of mercury poisoning have appeared in dental literature for the past few years. The most dangerous reality of this condition—one that is too often underemphasized—is that once the symptoms occur, a great deal of damage has been done. In my article entitled MERCURY POISONING—A CASE HISTORY, published in the Journal of the New Jersey Dental Association, Winter 1978, pages 10 and 11, I describe case studies where practitioners have been seriously and fatally injured due to prolonged exposure to mercury and mercury vapors.

The practitioner and the public in general is becoming aware of such problems and the resulting consequences. The federal government, concerned with the occupational exposure to inorganic mercury, has dealt with the problem in The Occupational Safety and Health Act of 1970 (OSHA). The National Institute for Occupational Safety and Health recommends an annual analysis for mercury for all individuals who handle mercury. Unfortunately, due to the pressures imposed by a dental practice and other considerations, such recommendations are not uniformly followed and hence, mercury poisoning continues to be a major problem.

The toxicity problem in dental offices arises from two sources. First, by direct contact and absorption through the skin and hence gloves are worn and recommended when handling mercury. A second major cause is through inhalation of mercury fumes or vapor. The fumes are generated when mercury volatizes during the mixing, grinding, mulling and cutting of the amalgam. There is both a hazard to the dentist and to his assistants and essentially, to any person handling mercury or alloys of the same.

As indicated, the consequences of mercury poisoning are substantial and result in severe changes in personality manifesting symptoms of anxiety, timidity, indecision, irritability or excitability. Persons suffer from headaches, fatique, drowsiness or insomnia; as well as vasomotor disturbances, tremors, speech disorders and many other serious and permanent disabilities.

The prior art is aware of such difficulties as evidenced by U.S. Pat. No. 4,059,903 issued on Nov. 29, 1977 and entitled a CONTROLLED ENVIRONMENT WORK ENCLOSURE by Meyer Piet and Dean Giles. This patent describes an enclosure which by the use of fans, maintains a subatmospheric pressure within the enclosure allowing air to be continuously drawn in through inlets and to be directed rapidly downward past and through the work platform and through a series of filters to attempt to eliminate the obnoxious fumes.

The enclosure described is relatively complicated and expensive to fabricate and relatively difficult to use. The enclosure employs access ports which accommodate flexible gloves to be used when working with the platform. This aspect as well as the air paths and so on create difficulty in operation and usage of that enclosure.

It is therefore an object of the present invention to provide an environmental enclosure adapted for use in dentistry for allowing one to handle mercury amalgam safely and expeditiously. The enclosure is simple to fabricate, easy to use and reliable in operation and inexpensive as compared to prior art devices.

BRIEF DESCRIPTION OF THE PREFERRED EMBODIMENT

An environmental enclosure apparatus for use in handling deleterious materials, comprising a base platform member having a central work area, a hollow housing having an opened bottom end relatively congruent with said work area of said platform for positioning said housing on said platform with said bottom end positioned over said central area, said housing having a top wall including an aperture located therein and at least one additional aperture in one of said sidewalls, a filter assembly removably positioned in said aperture in said top wall, said assembly including a selectively operated fan coupled to a filter housing for drawing air from the hollow of said housing via said filter housing when said fan is operative, elastic band means coupled to said additional aperture in said sidewall to allow insertion therethrough of a user's hand whereby access to said hollow of said housing can be achieved to mainly cause air on the outside of said housing to be drawn into said housing via said band coupled aperture.

BRIEF DESCRIPTION OF THE FIGURES

FIG. 1 is a front view of a vapor purifier enclosure according to this invention.

FIG. 2 is a partial sectional view taken through line 2—2 of FIG. 1.

FIG. 3 is a perspective view depicting a filter holder assembly and a mechanism for attaching the same to a fan housing.

DETAILED DESCRIPTION OF THE INVENTION

Figure 4:
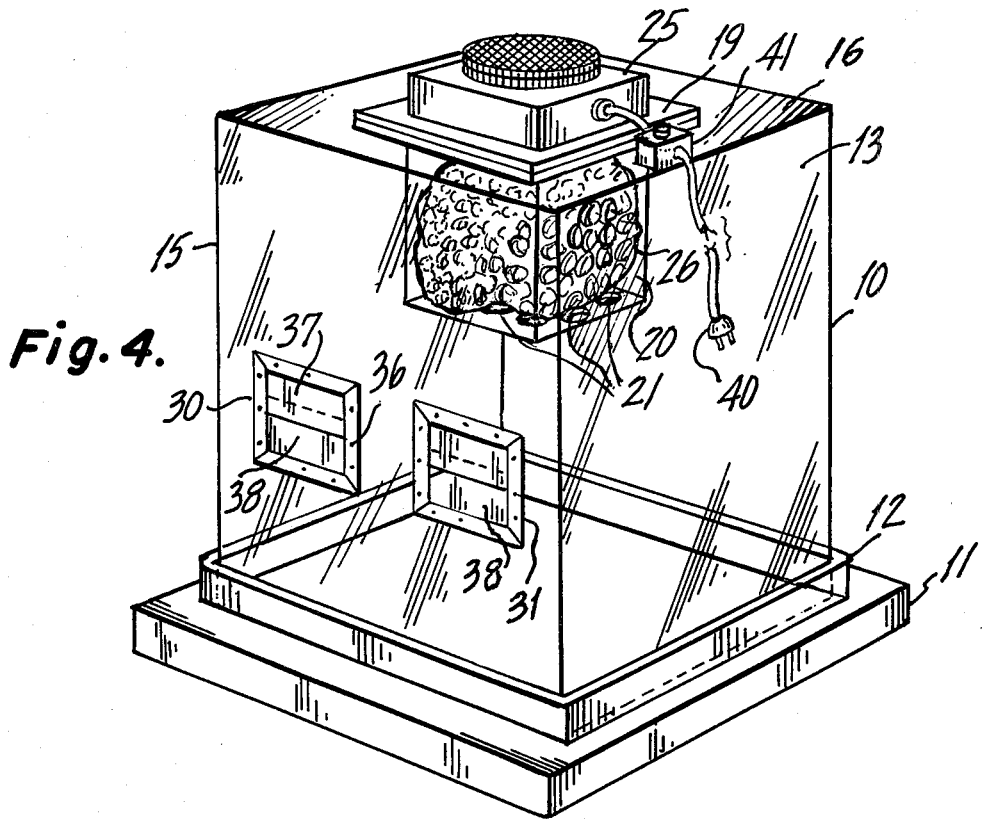
FIG. 4 is a perspective view of the enclosure according to this invention.

Referring to FIG. 1, there is shown a front perspective view of the environmental enclosure of the present invention. The enclosure is shown as rectangular in configuration, but it is understood that any other geometric configuration could be employed as well.

The enclosure consists of a top box-like portion 10 and a bottom platform assembly 11. The bottom assembly 11 is of a rectangular configuration and may be fabricated from a suitable material such as a metal, plastic or wood. The bottom assembly has a central work area. The work area is surrounded by a frame or flange 12 to prevent mercury spilled in the area to run out of the enclosure. The top housing 10 consists of a front wall 13, two sidewalls as 14 and 15, a back wall and a top wall 16. The walls of the housing as described may be fabricated from a clear plastic to enable a user to have relatively unobstructed visibility in regard to amalgam handling operations which, as will be explained, are performed within the hollow confines of the enclosure.

The top wall 16 has a relatively centrally located aperture 17 into which is inserted a fan 24 and filter assembly 18. The fan 25 is a rectangular unit which is available from many companies such as Rotron, Inc. of Woodstock, New York, Model No. WR 2A-1. Many other companies manufacture similar fan assemblies which can also be employed. Such fans are relatively flat and rectangular in shape. The fan is secured to a frame 19 which has an extending flange to enable it to be positioned on the top wall 16 as shown. The bottom opened end of the top assembly 10 fits within the frame 12 and hence, surrounds the work area.

A filter housing 20 is a hollow housing which is removably secured to the fan frame as will be explained and contains a plurality of apertures as 21 on the bottom surface. The apertures allow air within the housing to circulate through filter material due to the action of the fan 25. The filter consists of a plurality of charcoal pellets which are sulfur treated and commonly referred to as activated charcoal and which pellets are available from a plurality of manufacturers. A quantity of pellets are positioned within a mesh-like bag 26 which is similar in configuration and structure to a nylon stocking or nylon filter. The purpose of the bag 26 is to retain the filters within the desired volume inside the housing 20 as depicted in the figure. In this manner, the entire assembly 18 is inserted into the aperture 17 in the top wall 16 of the enclosure. If desired, it can be secured thereto by means of screws or other fasteners or can be inserted therein and retained based on the weight of the fan 25, the charcoal particles and the housing 20.

Shown and located in one of the walls are two inlet ports 30 and 31. These ports are indicated as rectangular in configuration but can be of any suitable geometric shape. The ports or apertures 30 and 31 are of sufficient size to enable a user to insert his hands into the hollow confines of the enclosure 10 to thereby enable the user to work with amalgam or mercury which is located within the housing and positioned on the top surface of the platform assembly 11. Each port has a frame member such as 35 associated therewith. The frame member is secured to the front wall 13 by means of suitable fasteners or screws as 36 and hence, the frame can be removed, if desired.

The frame has secured thereto two flexible bands such as 37 and 38. The bands are preferably fabricated from a relatively strong and flexible elastic material and overlap one another at the central portion. In this manner, the bands as shown and positioned prevent air from escaping through this path and most air will circulate through the filter 26 and through the fan when the unit is not in an operating position.

The fan 25 is conventionally energized by means of a power plug 40 adapted for insertion into an AC outlet. In series with the plug 40 is a switch 41 to enable a user to turn the fan on and off as desired.

Positioned within the housing there is shown an amalgamator 50. Basically an amalgamator is employed by a dentist or a practitioner to obtain the mercury alloy in various proportions for application to a patient's teeth and so on. The platform 12 is sufficiently large to enable the positioning of the amalgamator 50 thereon as well as various other tools and equipment used by a dentist to work with and handle amalgam.

Thus, as shown in FIG. 1, the unit basically is extremely simple and easy to construct. The fan and filter assembly 18 may be removed as desired from the aperture in the top wall 16. The housing 10 can be lifted and hence, the platform 11 can be cleaned and maintained at will.

It is also understood that the housing 10 as positioned on the platform 11 may contain a suitable flange or sealing material to thus further assure that an undue amount of air will not escape or enter through the space between the platform 11 and the housing 10, although some leakage is perfectly tolerable.

The operation of the device is as follows: The practitioner or his assistant inserts their gloved hands through the ports 30 and 31. The flexible bands 37 and 38 move inwardly to allow one to insert their hands as desired. Prior to doing so, the user will activate switch 41 and therefore energize the fan. The fan is arranged to direct the air from the hollow of the enclosure 10 through the filter 26 and hence, the charcoal particles and to expel air into the atmosphere via the fan assembly. The direction of air flow is shown in the diagram by the dashed line configurations.

As is seen, upon the insertion of a user's hands through the ports 30 and 31 air is drawn from the room or the outside environment as well as from the internal hollow of the housing through the filter and then the filtered air is discharged via the fan back into the room. In this manner, any obnoxious vapors emanating from the mercury are also forced through the filter where they are retained by the charcoal particles. The filter therefore completely filters the mercury fumes and the air emanating from the fan (air out) is relatively free from the obnoxious vapors and therefore does not permeate the the room, nor does it affect the practitioner or the user. Based on the air flow afforded by the arrangement, the mercury fumes are primarily directed through the filter and hence, the mercury vapors are completely filtered and removed from the air expelled via the fan 25.

Referring to FIG. 2, there is shown a pictorial representation depicting the action of the flexible bands 37 and 38 as secured by the frame 35. It is seen that as a user's hand is inserted into the aperture, the flexible bands stretch apart to enable the user to gain access to the internal hollow of the housing and hence, work with the amalgam contained therein as desired. The bands may be secured to the frame 35 by many well known techniques and can be replaced when they become worn or lose elasticity.

As above indicated, the user will employ gloves when working with the amalgam and can employ gloves which are particularly suited to the practitioner or his assistant which therefor enables a more efficient handling and working with the amalgam. It is also noted that if the user is thoroughly experienced in handling mercury, he may forego the use of gloves and peform the handling operations without the same.

Referring to FIG. 3, there is shown a perspective view of a filter accommodating housing as 20 of FIG. 1. As one can see, the bottom wall of the housing has suitable apertures 21 located therein. The housing 20 has an opened top to enable insertion of the charcoal particles as contained within the mesh-like bag member 26. The housing 20 may have a left and a right flange adjacent the opening to enable selective coupling to the fan frame by means of a suitable coupling scheme.

Depicted in FIG. 3 is a conventional coupling arrangement which employs projecting members 60 located on the fan assembly. The members 60 have a relatively enlarged head portion and a narrower central portion.

Located on the flanges of the housing 20 are suitable apertures as 61 which will allow insertion of the enlarged heads of member 60 into the apertures and then by moving the housing in the direction of the arrow, the central portions of the members 60 are constrained within the narrow slot portion of the aperture 61 to therefore enable one to remove the housing 20 as desired in order to change the charcoal particles or dispose of the same. It is therefore apprent that there are many alternate techniques for selectively coupling the housing 20 to the fan 25 or its frame to allow one to therefore selectively remove the housing in order to change the filter arrangement when it becomes saturated with mercury after prolonged use. Any such alternative coupling scheme is, of course, acceptable.

Referring to FIG. 4, there is shown a perspective diagram of the unit to generally depict the above described features. As indicated, the respective walls of the unit are preferably fabricated from a clear plastic to allow unobstructed vision for all directions. It is, of course, understood that the top wall or the side walls do not have to be fabricated from clear plastic, but any other material will also suffice as long as one has visual access to the working area provided by the platform. The flange 12 is shown as surrounding the central work area to prevent the escape of spilled mercury and to act as a seal.

It is also known that there are many techniques for fabricating or constructing the housing as depicted in FIGS. 1 and 4 and one may employ channels at the corners and so on to fabricate the structure shown.

As indicated above, it is sufficient to turn the fan on by means of the switch 41 prior to working with the amalgam located within the interior and this would be a normal procedure in using or working with the enclosure. In any event, there are many techniques which can be employed to provide for automatic fan operation when a user's hands are inserted into parts 30 and 31.

Figure 5:
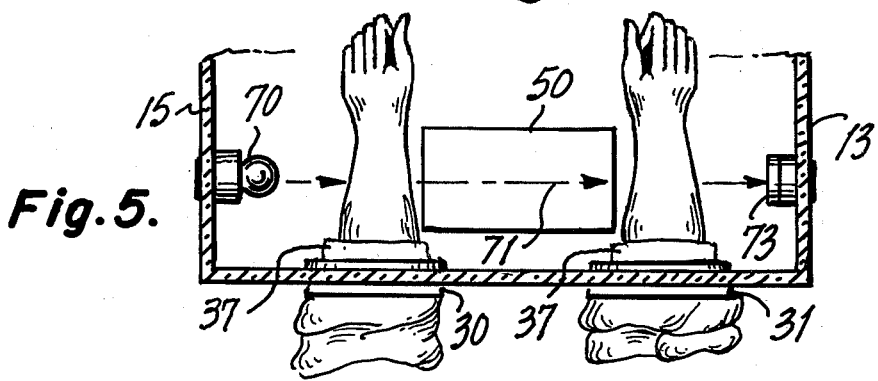
FIG. 5 is a partial top sectional view depicting an automatic fan control means.

Referring to FIG. 5, there is shown one embodiment to enable automatic operation of the fan. A user's hands are shown inserted via ports 30 and 31 and hence, are accessing the internal hollow of the housing. A light 70 is located on the right sidewall 15, while a photocell is located on the left sidewall 14. These may be positioned an inch or so from the ports 30 and 31 and relatively about the center line with the same. Hence, when the user inserts his hands into the hollow confines of the housing, the light beam 71 is broken or interrupted. Aligned with the light source 70 is a photodetector 73. When the beam of light is broken, the resistance of the photodetector increases and this automatically operates a relay which immediately energizes the fan. When the user's hands are removed, the light emanating from source 70 impinges upon the cell 73 and the fan is then turned off. This technique of employing a photocell to energize a relay is well known and is used in intrusion alarm systems and in a host of other applications as well.

Figure 6:
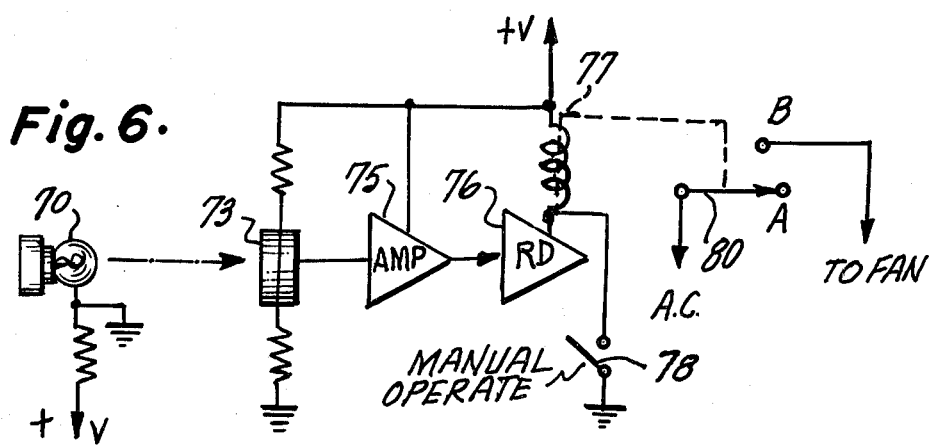
FIG. 6 is a circuit diagram having a light controlled fan actuator.

FIG. 6 shows a simple circuit to implement the above described operation. Essentially, the photocell 73 is connected in circuit with a suitable amplifier 75 having its output coupled to a relay driver 76. The coil 77 of a relay is activated by operation of the driver 76. A switch 78 is shown to enable manual operation of the fan, if it is desired and hence, automatic operation can be prevented by closing switch 78 to thereby operate the relay manually as desired. The relay coil is associated with a contact 80 having one terminal coupled to a source of AC power. When the relay is energized, the contact arm 80 moves from position A to position B and thus power is supplied to the fan to cause it to operate.

Thus, one can see that if the light beam between source 70 and photocell 73 is interrupted, the relay driver 76 will operate the relay to thereby energize the fan via contact B. Once the path between the source 70 and the cell 73 is restored by the removal of the user's hands, the fan is turned off. If mercury is being stored in the enclosure and it is desired to operate the fan, even though the mercury is not being handled, one may use the switch 78 to turn the fan on. The switch 78 thereby performs the same exact function as switch 41 and either the automatic or manual operation can be provided, as desired.

It is thus seen that the above described enclosure is relatively simple to fabricate and easy to use and maintain.

Various tests have been performed employing apparatus as depicted in the FIGS. and employed for amalgam handling in a dental facility. The present OSHA standard for exposure to mercury under normal conditions is 0.10 milligrams per cubic meter. However, the International Institute for Occupational Safety and Health has proposed lowering this standard to 0.05 milligrams per cubic meter.

Measurements made inside the enclosure with the fan off detected mercury vapor at a level of 0.09 milligrams per cubic meter which is well above the suggested limits. When the fan was turned on, the level within the enclosure fell to 0.02 milligrams per cubic meter. The air which was discharged by the fan (air out) had a level of 0.02 milligrams per cubic meter. This reading was taken while a practitioner was performing an amalgam mixing inside the enclosure. When amalgam is being mixed, the level of mercury vapor inside the enclosure was far greater than 1.0 milligrams per cubic memter, which is an extremely dangerous level.

The use of the enclosure enabled the reduction of mercury in the surrounding atmosphere to be below 0.02 milligrams per cubic meter. Hence, the disclosure described reduced mercury vapor content in the atmosphere by at least eighty percent. The enclosure therefore protects the dentist and his assistant and the atmosphere from contamination by mercury in the handling of amalgam by containing all the components necessary within the enclosure.

The apparatus employed activated charcoal within the mesh-like bag to a depth of approximately three to four inches and at this level, reduced the mercury vapor between eighty to ninety percent. It is thus seen that the enclosure provided reduces mercury vapor directly at its source and enables the practitioner to handle the amalgam without fear of contamination by inhalation.

As shown and described, the unit is extremely reliable in operation, simple to use and to construct and thus can be employed in most operations using mercury or other hazardous materials without fear of contamination in regard to outside environment.

Many modifications and alternative constructions will be discerned by one skilled in the art in regard to modifying individual parts or components in order to accommodate various uses and conditions. All such modifications may be made without departing from the scope and extent of the claims appended hereto.

I claim:

1. An environmental enclosure apparatus for use in handling deleterious materials, comprising:
 (a) a base platform member having a central work area, (b) a hollow housing having an opened bottom end relatively congruent with said work area of said platform for positioning said housing on said platform with said bottom end positioned over said central area, said housing having a top wall including an aperture located therein and at least one additional aperture in one of said sidewalls, (c) a filter assembly removably positioned in said aperture in said top wall, said assembly including a selectively operated fan coupled to a filter housing for drawing air from the hollow of said housing via said filter housing when said fan is operative, (d) elastic band means coupled to said additional aperture in said sidewall to allow insertion therethrough of a user's hand whereby access to said hollow of said housing can be achieved to mainly cause air on the outside of said housing to be drawn into said housing via said band coupled aperture wherein said elastic band means comprises a first band of elastic material positioned across a top portion of said aperture, a second band of elastic material positioned across a bottom portion of said aperture, with said first and second bands overlapping at a relatively central portion of said aperture to permit insertion of a user's hand therein.

2. The enclosure according to claim 1 wherein said filter housing contains a plurality of activated charcoal pellets for absorbing any obnoxious fumes present within said hollow of said housing.

3. The enclosure according to claim 1 wherein said deleterious material is dental amalgam containing mercury, said central area being surrounded by a flange to enable said opened bottom end of said hollow housing to fit within said flange when said hollow housing is positioned upon said platform.

4. The enclosure according to claim 1 wherein said filter housing is selectively coupled to said fan to enable selective removal of said housing from said fan.

5. The apparatus according to claim 1 further including means responsive to the insertion of a user's hand into said additional aperture for selectively operating said fan.

6. The apparatus according to claim 1 further including means coupled to said fan for selectively operating the same as desired.

7. The apparatus according to claim 1 wherein at least said one sidewall containing said additional aperture is fabricated from a clear plastic.

8. The apparatus according to claim 2 further comprising a bag fabricated from a mesh-like material for retaining said charcoal pellets within said filter housing, 9. The apparatus according to claim 4 wherein said filter housing is a hollow rectangular housing having an opened top with a bottom wall having a plurality of air circulating apertures, and means coupled to said top of said housing adjacent said opening for selectively coupling the same to said fan.

10. An environmental enclosure apparatus for use in handling deleterious materials, comprising:
(a) a base platform member having a central work area,
(b) a hollow housing having an opened bottom end relatively congruent with said work area of said platform for positioning said housing on said platform with said bottom end positioned over said central area, said housing having a top wall including an aperture located therein and at least one additional aperture in one of said sidewalls,
(c) a filter assembly removably positioned in said aperture in said top wall, said assembly including a selectively operated fan coupled to a filter housing for drawing air from the hollow of said housing via said filter housing when said fan is operative,
(d) elastic band means coupled to said additional aperture in said sidewall to allow insertion therethrough of a user's hand whereby access to said hollow of said housing can be achieved to mainly cause air on the outside of said housing to be drawn into said housing via said band coupled aperture, and
(e) means responsive to the insertion of a user's hand into said additional aperture for selectively operating said fan.

* * * * *